United States Patent [19]

Baylis

[11] Patent Number: 5,488,171
[45] Date of Patent: Jan. 30, 1996

[54] PHOSPHINATE ESTERS

[75] Inventor: Eric K. Baylis, Stockport, England

[73] Assignee: Ciba-Geigy Corporation, Ardsley, N.Y.

[21] Appl. No.: 203,961

[22] Filed: Feb. 28, 1994

[30] Foreign Application Priority Data

Mar. 6, 1993 [GB] United Kingdom .................. 9304619

[51] Int. Cl.⁶ ..................................................... C07F 9/02
[52] U.S. Cl. ................................................................ 568/8
[58] Field of Search ..................................................... 568/8

[56] References Cited

FOREIGN PATENT DOCUMENTS 181833  5/1986  European Pat. Off. .

OTHER PUBLICATIONS

CA116:59480 (1991), Cmpd. Reg. Nos. 138568–44–2 P & 138568–45–3P.
Chem. Abst. 97 (5):39019r (1982).
C. Marie, Ann. Chim. Phys. (1904) pp. 335, 368, 369, 370 & 371.
S. J. Fitch "Hypophosphite Esters from Orthocarbonyls" Jan. 5, 1964, pp. 61–64 vol. 86.
C. Marie —Comptes Rendus Hebdomadaires Des Seances De l'Academie Des. Sciences, Serie C: Sciences Chimiques vol. 34, 1902, pp 286–288.

Primary Examiner—James H. Reamer
Assistant Examiner—Michael B. Hydorn
Attorney, Agent, or Firm—George R. Dohmann

[57] ABSTRACT

A compound of formula

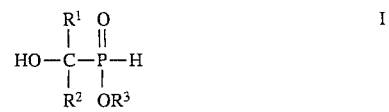

where $R^1$ and $R^2$ are independently a $C_1$–$C_{10}$ aliphatic radical, or $R^1$ is a $C_1$–$C_{10}$ aliphatic radical and $R^2$ is a $C_6$–$C_{10}$ aromatic radical, and $R^3$ is a $C_1$–$C_8$ aliphatic radical, a $C_3$–$C_8$ cycloaliphatic radical, a $C_6$–$C_{15}$ aromatic radical or a $C_7$–$C_{13}$ araliphatic radical, provided that $R^3$ is not methyl when $R^1$ and $R^2$ are each methyl, that $R^3$ is not ethyl when $R^1$ and $R^2$ are each methyl and that $R^2$ is not p-aminophenyl when $R^1$ is methyl and $R^3$ is ethyl.

17 Claims, No Drawings

PHOSPHINATE ESTERS

This invention relates to phosphinate esters, their preparation and their use in synthesis.

Phosphinate esters having a reactive P-H group and a protected P-H group have been used in the synthesis of pharmaceutically active substances such as the substituted propane-phosphonous compounds described in EP 0181833. In synthesis, the protected P-H group generally has be to converted into a P-H group after reaction of the protected phosphinate ester with another compound. With the known protected phosphinate esters previously used in such synthesis, the protecting group has had to be removed by hydrolysis under acid conditions. This imposes a limitation on the use of such protected phosphinate esters, since they cannot be used where hydrolysis under acid conditions would have an undesirable effect on other groups present.

It has now been found that certain phosphinates having a reactive P-H bond and a protected P-H bond, many of which are novel, can be reacted with compounds having at least one group reactive with a P-H bond to give products from which the protecting group can be removed by hydrolysis under mild basic conditions.

Accordingly, the present invention provides, in one aspect, a compound of formula

where $R^1$ and $R^2$ are independently a $C_1$–$C_{10}$ aliphatic radical, or $R^1$ is a $C_1$–$C_{10}$ aliphatic radical and $R^2$ is a $C_6$–$C_{10}$ aromatic radical, and $R^3$ is a $C_1$–$C_8$ aliphatic radical, a $C_3$–$C_8$ cycloaliphatic radical, a $C_6$–$C_{15}$ aromatic radical or a $C_7$–$C_{13}$ araliphatic radical, provided that $R^3$ is not methyl when $R^1$ and $R^2$ are each methyl, that $R^3$ is not ethyl when $R^1$ and $R^2$ are each methyl and that $R^2$ is not p-aminophenyl when $R^1$ is methyl and $R^3$ is ethyl.

Generally, in compounds of formula I as hereinbefore defined, $R^1$ and $R^2$ are independently $C_1$–$C_{10}$ alkyl, which may be unsubstituted or substituted, for example by halogen, preferably fluorine or chlorine, or $R^1$ is such a group and $R^2$ is a $C_6$–$C_{10}$ aryl group, which may be unsubstituted or substituted, for example by halogen.

$R^1$ or $R^2$ as unsubstituted or substituted $C_1$–$C_{10}$ alkyl may be, for example, methyl, ethyl, n-propyl, isopropyl, n-butyl, isobutyl, tert-butyl, n-pentyl, neopentyl, n-hexyl, n-heptyl, n-octyl, 2-ethylhexyl, n-nonyl or n-decyl, or any of these groups substituted by halogen, for example 2-fluoroethyl, 2,2,2-trifluoroethyl, trichloromethyl, 2-chloroethyl, 2,2,2-trichloroethyl, or 2-chloro-n-propyl. $R^2$ as $C_6$–$C_{10}$ aryl may be, for example, phenyl, o-tolyl, m-tolyl, p-tolyl, 2,3-dimethylphenyl, 2,4-dimethylphenyl, 2,5-dimethylphenyl, alpha-naphthyl or beta-naphthyl. Preferably, $R^1$ and $R^2$ are independently $C_1$–$C_8$ alkyl, or $R^1$ is $C_1$–$C_8$ alkyl and $R^2$ is $C_6$–$C_8$ aryl. In certain especially preferred compounds, $R^1$ and $R^2$ are each methyl, or $R^1$ is methyl and $R^2$ is n-hexyl, isobutyl or p-tolyl.

In formula I, $R^3$ is generally $C_1$–$C_8$ alkyl, which may be unsubstituted or substituted by, e.g., $C_1$–$C_4$ alkoxy, $C_1$–$C_4$ alkyl sulphonyl, cyano or halogen; $C_3$–$C_8$ cycloalkyl, which may be unsubstituted or substituted e.g. by $C_1$–$C_4$ alkoxy or halogen; $C_6$–$C_{15}$ aryl, which may be unsubstituted or substituted e.g. by halogen, $C_1$–$C_4$ alkoxy or nitro; or $C_7$–$C_{13}$ aralkyl, which may be unsubstituted or substituted e.g. by $C_1$–$C_4$ alkoxy or halogen.

$R^3$ as unsubstituted or substituted $C_1$–$C_8$ alkyl may be straight chain or branched, for example, methyl, ethyl, n-propyl, isopropyl, n-butyl, isobutyl, tert-butyl, n-pentyl, neopentyl, n-hexyl, n-heptyl, n-octyl, 2-ethylhexyl, or any of these groups substituted by methoxy, ethoxy, n-propoxy, isopropoxy, n-butoxy, methanesulphonyl, cyano, bromine, chlorine or fluorine such as methoxymethyl, 2-methoxyethyl, 2-ethoxymethyl, 2-n-butoxyethyl, 3-methoxypropyl, 1-methoxybutyl, 2-methoxybutyl, methanesulphonylmethyl, 2-methanesulphonylethyl, 2-cyanoethyl, 2-fluoroethyl, 2,2,2-trifluoroethyl, trichloromethyl, 2-chloroethyl,1-(chloromethyl) ethyl, 2,2,2-trichloroethyl, 2-chloro-n-propyl or 3-chloro-n-butyl.

$R^3$ as unsubstituted or substituted $C_3$–$C_8$ cycloalkyl may be, for example, cyclopropyl, cyclobutyl, cyclopentyl, methylcyclopentyl, cyclohexyl, methylcyclohexyl, dimethylcyclohexyl, cycloheptyl or cyclooctyl, preferably cyclohexyl, or any of these groups substituted by methoxy, ethoxy, n-propoxy, isopropoxy, n-butoxy, cyano, chlorine or fluorine.

$R^3$ as unsubstituted or substituted $C_6$–$C_{15}$ aryl may be, for example, phenyl, o-tolyl, m-tolyl, p-tolyl, o-xylyl, m-xylyl, p-xylyl, alpha-naphthyl or beta-naphthyl, or any of these groups substituted by halogen, $C_1$–$C_4$ alkoxy or nitro. Preferably, $R^3$ as $C_6$–$C_{15}$ aryl is $C_6$–$C_8$ aryl, especially phenyl.

$R^3$ as unsubstituted or substituted $C_7$–$C_{13}$ aralkyl may be, for example, benzyl, 4-methylbenzyl, o-methoxybenzyl, p-methoxybenzyl, diphenylmethyl, 2-phenylethyl, 2-phenylpropyl or 3-phenylpropyl, preferably $C_7$–$C_9$ aralkyl, especially benzyl.

In one preferred class of compounds of formula I, $R^3$ is $C_1$–$C_6$ alkyl, which is unsubstituted or substituted by cyano, halogen or $C_1$–$C_4$ alkoxy, especially methyl, ethyl, n-butyl, 2-cyanoethyl, 1-(chloromethyl) ethyl or 2-methoxyethyl. In another preferred class, $R^3$ is branched alkyl, preferably $C_2$–$C_6$ branched alkyl, especially isobutyl. In a further preferred class of compounds of formula I, $R^3$ is $C_5$ to $C_7$ cycloalkyl or $C_6$ to $C_8$ aryl, especially cyclohexyl or phenyl.

In especially preferred classes of compounds of the invention, $R^1$ and $R^2$ are each methyl and $R^3$ is ethyl, n-butyl or isobutyl; or $R^1$ is methyl, $R^2$ is isobutyl and $R^3$ is 2-methoxyethyl, cyclohexyl or phenyl; or $R^1$ is methyl, $R^2$ is n-hexyl and $R^3$ is 2-cyanoethyl; or $R^1$ is methyl, $R^2$ is p-tolyl and $R^3$ is 1-(chloromethyl)ethyl.

Compounds of formula I may be prepared by esterifying a phosphonous (phosphinic) acid of formula

with an alcohol of formula $R^3OH$, where $R^1$, $R^2$ and $R^3$ are as hereinbefore defined.

The esterification reaction may be carried out at $-10°$ to $40°$ C., preferably $0°$ to $20°$ C. It is conveniently effected in an organic solvent, for example a hydrocarbon such as toluene or, preferably, an ether such as diethyl ether, dioxan or, especially, tetrahydrofuran. The reaction is preferably carried out in the presence of a basic catalyst, usually a tertiary amine such as dimethylaminopyridine, and a dehydrating condensation agent such as $N,N^1$-dicyclohexylcarbodiimide. A suitable procedure is described by Karanewsky and Badia, Tetrahedron Letters, 27,1751 (1986).

Compounds of formula I may be prepared by esterifying a phosphonous acid of formula II by reaction with a chloroformate of formula $ClCOOR^3$ where $R^3$ is as hereinbefore defined. This method can be useful where the chloroformate is commercially available, e.g. in the cases of methyl, ethyl, isopropyl, isobutyl, 2-bromoethyl, 2,2,2-chloroethyl, phenyl and benzyl chloroformates. It is conveniently carried out in an organic solvent in the presence of a base, preferably a tertiary amine such as triethylamine, using the procedure described by Hewill, Aust. J. Chem. 32,463(1979). It may be effected at −20° to 40° C., preferably 0° to 20° C.

Phosphonous acids of formula II can be prepared by reaction of hypophosphorous acid (phosphinic acid) with a ketone of formula

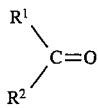

$$\begin{array}{c} R^1 \\ \phantom{R^1}\diagdown \\ \phantom{R^1R^2}C{=}O \\ \diagup \\ R^2 \end{array} \qquad \text{III}$$

where $R^1$ and $R^2$ are as hereinbefore defined, in the presence of an acid catalyst, for example using an adaptation of the procedures described by C. Marie, C.r.134,288 and Ville J. Ann. Chim. Phys. [6] 23,289 (1891). When $R^1$ and $R^2$ are both methyl, i.e. where the ketone is acetone, dimers form and the separation of the products is difficult. Where $R^1$ and $R^2$ are not both methyl, particularly where $R^1$ and $R^2$ are different, dimers are generally not formed.

Phosphonous acids of formula II can also be prepared by hydrolysis of an ester of formula

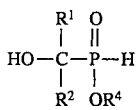

$$\begin{array}{c} R^1 \;\; O \\ | \;\;\; \| \\ HO{-}C{-}P{-}H \\ | \;\;\; | \\ R^2 \; OR^4 \end{array} \qquad \text{IV}$$

where $R^1$ and $R^2$ are as hereinbefore defined and $R^4$ is $C_1$–$C_4$ alkyl, preferably methyl or ethyl. This hydrolysis can be effected by heating with water, acid or base.

Esters of formula IV can be prepared by reaction of hypophosphorous acid with a ketal of formula

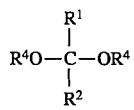

$$\begin{array}{c} R^1 \\ | \\ R^4O{-}C{-}OR^4 \\ | \\ R^2 \end{array} \qquad \text{V}$$

where $R^1$, $R^2$ and $R^4$ are as hereinbefore defined, for example using the procedure described by S. J. Fitch, J. Amer. Chem. Soc. 86, 61 (1964).

Compounds of formula I can also be prepared by reaction of hypophosphorous acid with a ketal of formula

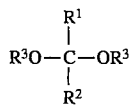

$$\begin{array}{c} R^1 \\ | \\ R^3O{-}C{-}OR^3 \\ | \\ R^2 \end{array} \qquad \text{VI}$$

where $R^1$, $R^2$ and $R^3$ are as hereinbefore defined, for example using the procedure described in the abovementioned paper by S. J. Fitch.

Ketals of formula V or VI are either commercially available or may be prepared by known procedures. For example, where $R^1$ and $R^2$ are methyl, ketals of formulae V or VI where $R^4$ or $R^3$ respectively has at least 3 carbon atoms can be prepared from acetone dimethyl ketal by transketalisation using an alcohol of formula $R^4OH$ or $R^3OH$ in the presence of an acid as catalyst. A suitable procedure is described by Loretie and Howard, J. Org. Chem. 25,521 (1960).

Compounds of formula I can be prepared by reacting an alkyl phosphinate (hypophosphite) of formula

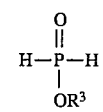

$$\begin{array}{c} O \\ \| \\ H{-}P{-}H \\ | \\ OR^3 \end{array} \qquad \text{VII}$$

with a ketone of formula III, where $R^3$ is as hereinbefore defined, for example under the conditions described by S. J. Fitch, J. Amer. Chem. Soc. 86,61.(1964).

Compounds of formula I can also be prepared by reacting an alkyl hypophosphite of formula VII, generally at ambient temperature, with a silylating agent, preferably a dialkylhalosilane or trialkylhalosilane such as dimethylchlorosilane, trimethylchlorosilane or triethylchlorosilane, in the presence of a base, preferably a tertiary amine, to form a P(III) silyl compound which, where the silylating agent is a dialkylhalosilane or a trialkylhalosilane, is of formula VIII or VIIIA respectively

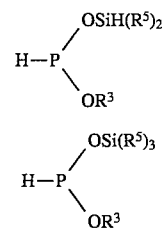

$$\begin{array}{c} \phantom{H}\diagup OSiH(R^5)_2 \\ H{-}P \\ \phantom{H}\diagdown OR^3 \end{array} \qquad \text{VIII}$$

$$\begin{array}{c} \phantom{H}\diagup OSi(R^5)_3 \\ H{-}P \\ \phantom{H}\diagdown OR^3 \end{array} \qquad \text{VIIIA}$$

where $R^5$ is a $C_1$–$C_4$ alkyl group, and reacting the P(III) silyl compound with a ketone of formula III, generally at a temperature of 30°–90° C., preferably 50° to 70° C.

Alkyl hypophosphites of formula VII can be prepared by reacting hypophosphorus acid with a corresponding alkyl orthocarboxylate, usually orthoformate, for example using the procedure described by S. J. Fitch, J. Amer. Chem. Soc. 86,61(1964), or by reacting hypophosphorous acid with a corresponding alkyl chloroformate in the presence of a base, usually a tertiary amine.

Compounds of formula I where $R^1$, $R^2$ and $R^3$ are as hereinbefore defined, and compounds of formula I where the definitions of $R^1$, $R^2$ and $R^3$ are not subject to the provisos hereinbefore stated, are useful in the synthesis of pharmaceutically active substances by reaction with compounds having at least one group reactive with a P-H bond. Accordingly, the present invention also provides use of a compound of formula

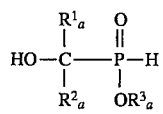

$$\begin{array}{c} R^1_a \;\; O \\ | \;\;\; \| \\ HO{-}C{-}\!\!-\!\!-P{-}H \\ | \;\;\; | \\ R^2_a \; OR^3_a \end{array} \qquad \text{IA}$$

where $R^1_a$ and $R^2_a$ are independently a $C_1$–$C_{10}$ aliphatic radical, or $R^1_a$ is a $C_1$–$C_{10}$ aliphatic radical and $R^2_a$ is a $C_6$–$C_{10}$ aromatic radical, and $R^3_a$ is a $C_1$–$C_8$ aliphatic radical, a $C_3$–$C_8$ cycloaliphatic radical, a $C_6$–$C_{15}$ aromatic radical or a $C_7$–$C_{13}$ araliphatic radical, for the synthesis of an organophosphorus compound by reaction of the compound of formula IA with an organic compound having at least one group reactive with a P-H bond.

$R^1_a$, $R^2_a$ and $R^3_a$ may be chosen from the same groups as $R^1$, $R^2$ and $R^3$ respectively, free from the provisos hereinbefore stated with respect to the definitions of $R^1$, $R^2$ and $R^3$ in formula I, i.e. $R^1_a$, $R^2_a$ and $R^3_a$ can each be methyl, $R^1_a$ and $R^2_a$ can each be methyl when $R^3_a$ is ethyl and $R^2_a$ can be p-aminophenyl when $R^1$ is methyl and $R^3$ is ethyl.

Compounds of formula IA which are also compounds of formula I can be prepared as hereinbefore described. Compounds of formula IA where $R^1_a$, $R^2_a$ and $R^3_a$ are each methyl can be prepared as described by S. J. Fitch, J. Amer. Chem. Soc. 86,61 (1964). Compounds of formula IA where $R^1$ and $R^2$ are methyl and $R^3$ is ethyl can be prepared as described by C. Marie, A. ch. [8], 3, 370.

In synthetic procedures, the reaction product of the compound of formula IA and the compound having a group reactive with P-H, or derivatives of this reaction product in which the protecting $HO{-}C(R^1_a)R^2_a{-}$ group derived from the compound of formula IA is retained, may be reacted with a hydrolysing agent to remove this protecting group and generate a P-H bond when desired. It has surprisingly been found that such deprotection can be effected by hydrolysis with a base, usually by heating with aqueous ammonia at temperatures from ambient to 100° C., preferably 70°–90° C.

The compound having one or more groups reactive with a P-H bond may be, for example, a compound having at least one aldehyde or ketone group or a compound having at least one ethylenic double bond. Sugars having such reactive groups are particularly useful in the synthesis of compounds having antiviral activity. In accordance with the invention, the compound having at least one group reactive with a P-H bond is preferably a compound having an ethylenic double bond, especially a sugar having such a double bond.

In one particularly useful synthesis, for example, a compound of formula I is reacted, in the presence of a free radical initiator, with an olefinic sugar acetonide of formula

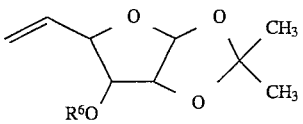

where $R^6$ is hydrogen, substituted or unsubstituted $C_1$–$C_{10}$ alkyl, $C_2$–$C_{10}$ alkenyl, $C_6$–$C_{15}$ aryl or $C_7$–$C_{16}$ aralkyl, $R^7CO$— where $R^7$ is substituted or unsubstituted $C_1$–$C_{10}$ alkyl, $C_2$–$C_{10}$ alkenyl, $C_3$–$C_8$ cycloalkyl, $C_6$–$C_{15}$ aryl or $C_7$–$C_{16}$ aralkyl, or $R^5$ is silyl substituted by three $C_1$–$C_{15}$ hydrocarbyl groups, to give a compound of formula

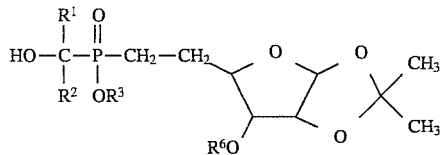

where $R^1$, $R^2$, $R^3$ and $R^6$ are as hereinbefore defined.

Suitable initiators include azo compounds such as azobis(isobutyronitrile), peroxides such as benzoyl peroxide, tert-butyl peroxide or 2,2-bis (tert-butylperoxy)propane, peresters such as tert-butyl perbenzoate or tert-butyl per-2-ethylhexanoate, percarbonates such as diacetyl perdicarbonate or bis(4-tert-butylcyclohexyl)perdicarbonate or persalts such as potassium persulphate. The initiator is generally used in an amount of 0.1 to 100 mol. %, preferably 5 to 15 mol %, per mol of the olefinic compound of formula IX. The reaction may be carried out without a solvent, but is preferably carried out in an organic solvent, usually an aromatic hydrocarbon such as benzene, toluene or xylene. It may be carried out at temperatures of 30° to 100° C., preferably 70° to 90° C.

Compounds of formula X may be converted, by reaction with a hydrolysing agent for the acetonide group, for example an acidic ion exchange resin, followed by esterification with an acid of formula $R^8COOH$ or an anhydride or acyl halide thereof, into compounds of formula

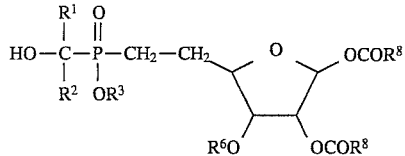

where $R^8$ is substituted or unsubstituted $C_1$–$C_{10}$ alkyl, $C_2$–$C_{10}$ alkenyl, $C_3$–$C_8$ cycloalkyl, $C_6$–$C_{15}$ aryl or $C_7$–$C_{16}$ aralkyl and $R^1$, $R^2$, $R^3$ and $R^6$ are as hereinbefore defined.

Compounds of formula XI may be converted, by glycosylation with nucleoside bases such as thymine, into nucleotide analogues of formula

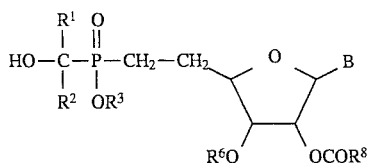

where B is a nucleoside base radical such as thyminyl, and $R^1$, $R^2$, $R^3$, $R^6$ and $R^8$ are as hereinbefore defined.

This reaction may be carried out using known glycosylation procedures, for example in the presence of a silylating agent such as trimethylsilyl chloride, bis(trimethylsilyl)acetamide or hexamethyldisilazane and a catalyst such as a fluoralkanesulphonate salt in an organic solvent such as acetonitrile or 1,2-dichloroethane at a temperature of 40°–90° C. followed by treatment with an aqueous acid, usually an organic acid such as acetic acid, to regenerate the tertiary hydroxyl group which has become silylated during the glycosylation reaction.

Compounds of formula XII where $R^6$ is $R^7CO$— can be converted, by basic hydrolysis of the $R^7COO$— and $R^8COO$— groups using, for example, potassium carbonate in methanol, followed by removal of the P-H protecting group by hydrolysis with aqueous ammonia, suitably at 70°–90° C., followed by acidification, into nucleotide analogues of formula

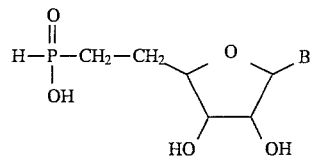

where $R^3$ and B are as hereinbefore defined.

Compounds of formula XIII can be reacted, through the deprotected P-H bond, after suitable protection of the OH groups, with nucleotide analogues having an aldehyde group or ethylenic double bond to give dinucleotide analogues having antiviral properties.

Olefinic sugar acetonides of formula IX can be prepared by reaction of 1,2,5,6-di-O-isopropylidene-α-D-allofuranose (prepared as described in Carbohyd. Res. 24 (1972) 192) with a compound of formula $R^6_aX$ or $(R^6_aCO)_2O$ where $R^6_a$ is the same as $R^6$ except that $R^6_a$ cannot be hydrogen and X is a halogen atom or a hydroxyl group, to etherify or esterify the hydroxyl group on the furanose ring, reacting the product with 80% acetic acid at ambient temperature to hydrolyse the acetonide group, reacting the hydrolysis product with methanesulphonyl chloride in the presence of a base to replace both hydroxyl groups by methane sulphonyloxy groups, and reacting the dimethanesulphonyloxy product with sodium iodide in methyl ethyl ketone at 70°–90° C., to give an acetonide of formula IX in which $R^6$ is $R^6_a$, which can be hydrolysed by treatment with potassium carbonate in aqueous methanol at ambient temperature to give an acetonide of formula IX in which $R^6$ is hydrogen.

The invention is illustrated by the following Examples.

EXAMPLE 1

Commercial hypophosphorous acid (50%) is concentrated to 94% on a rotary evaporator. A mixture of hypophosphorous acid (94%, 210.6 g, 3M) and 2,2-dimethoxypropane (917 g, 8.8M) is allowed to stand at room temperature for 6 days. The mixture is evaporated under vacuum and distilled on a wiped-wall still to give methyl(1-hydroxy-1-methylethyl)phosphinate (268 g, 65%, b.p. 65° C./0.1 mm).

$^{31}$p nmr (CDCl$_3$, 24.15 MHz) δ=45 ppm, J$_{PH}$ 545 Hz. (Fitch.J.Amer. Chem.Soc. 1964, 86, 61).

The methyl (1-hydroxy-1-methylethyl)phosphinate prepared as described immediately above is heated with water (1 l) on a steam bath for 8 hours until conversion to 1-hydroxy-1-methylethylphosphonous acid is complete (monitored by $^{31}$P nmr). The water is removed on a rotary evaporator and the residue is completely dried by co-evaporation with toluene. A sample of this phosphonous acid (4.6 g, 0.037M), isobutyl alcohol (3.02 g, 0.041M) and dimethylaminopyridine (0.5 g, 0.0041M) is stirred at 5° C. in tetrahydrofuran. Dicyclohexylcarbodiimide (8.4 g, 0.041M) is added portionwise over 30 minutes. On completion of the reaction ($^{31}$ P nmr), ether (50 ml) is added and the precipitated dicyclohexyl urea is filtered off. Evaporation of the ether liquors gives a pale yellow oil (6.7 g) which is purified by chromatography on silica using ether, then ethyl acetate, as eluant to give isobutyl(1-hydroxy-1-methylethyl)phosphinate.

Found: C 47.0, H 9.5, P 17.1%; C$_7$H$_{17}$O$_3$P requires C 46.7, H 9.5, P 17.2%.

$^{31}$P nmr (CDCl$_3$, 162 MHz) δ=42.2 ppm.

EXAMPLE 2

2,2-Diethoxypropane (3.96 g, 0.03M) and hypophosphorous acid (100%, 0.66 g, 0.01M) are allowed to stand at room temperature for 5 days. The mixture is distilled on a wiped-wall still to give ethyl(1-hydroxy-1-methylethyl)phosphinate, (b.p. 70°/0.3 mm).

$^{31}$P nmr (CDCl$_3$, 36.21MHz) δ=41.6 ppm.

Found: C 39.4, H 8.6, P 20.4%; C$_5$H$_{13}$O$_3$ P requires C 39.5, H 8.6, P 20.8%.

EXAMPLE 3

Hypophosphorous acid (100%, 2.0 g, 0.03M) and ethyl chloroformate (3.3 g, 0.03M) are stirred under nitrogen at room temperature in THF (40 ml). Triethylamine (3.03 g, 0.03M) is carefully added with cooling over 1 hour. $^{31}$P nmr shows that there is 85% conversion to ethyl hypophosphite ($^{31}$ P nmr δ=16 ppm). Trimethylsilyl chloride (3.3 g, 0.3M) is added followed by triethylamine (3.03 g, 0.03M). The mixture is stirred for 1 hour, when conversion to ethyltrimethylsilyl phosphinate ($^{31}$P nmr δ=149 ppm) is complete. Acetone (5 ml) is added and the mixture is stirred for 1 hour at 60° C. The mixture is then cooled, quenched with water and washed with methylene chloride. The aqueous phase is evaporated and the residual gum is stirred with ether. Evaporation of the ether gives ethyl (1-hydroxy-1-methylethyl)phosphinate after distillation.

EXAMPLE 4

A mixture of 2,2-dimethoxypropane (31.2 g, 0.3M), n-butanol (48.9 g, 0.66M) and toluene-p-sulphonic acid (0.05 g) is heated at 110° C., removing a fraction boiling below 60° C. over 2 hours. The mixture is cooled, brought to pH 9 with sodium methoxide in methanol, then distilled to give acetone di-n-butylketal b.p. 80° C./15 mm Hg, (33.8 g 60%). A sample of this ketal (18.8 g 0.1 m) and hypophosphorous acid (2.2 g, 0.033M) are stirred at room temperature for 7 days. Fractional distillation gives n-butyl (1-hydroxy-1-methylethyl)phosphinate (b.p. 84° C./0.3 mm Hg).

$^{31}$P nmr (CDCl$_3$ 36.21 MHz) δ=44.4 ppm.

EXAMPLE 5

1-hydroxy-1-methylethylphosphonous acid, prepared as described in Example 1, (9.92 g, 0.08M) is dissolved in dichloromethane (100 ml) at 0° C. and isobutyl chloroformate (21.85 g, 0.16M) is added in one portion. Triethylamine (16.19 g, 0.16M) is added dropwise over 1 hour maintaining the temperature at 0° C. The mixture is allowed to warm to room temperature, the precipitated solid is filtered off and the filtrate is evaporated to an oil. This oil is distilled on a wiped-wall still to give isobutyl(1-hydroxy-1-methylethyl)phosphinate (b.p. 76°–8° C./0.1 mm Hg)

$^{31}$P nmr (CDCl$_3$, 162 MHz) δ=42.2 ppm, J$_{PH}$=532.8 Hz.

EXAMPLE 6

A mixture of octan-2-one (3.76 g, 0.29M) and hypophosphorus acid (91.5%, 2.09 g, 0.029M) is heated at 100° C. for 12 hours in the presence of Dowex 50W x 2 ion exchange resin (1 ml, aqueous slurry). The mixture is cooled to room temperature, methanol (50 ml) is added and the Dowex is removed by filtration. The filtrate is evaporated to an oily residue, which is dissolved in ethyl acetate, washed with water, brine, then dried (MgSO$_4$). Removal of the solvent gives 1-hydroxy-1-methylheptylphosphonous acid.

$^{31}$p NMR (CDCl$_3$, 162MHz) δ=39 ppm. J.$_{PH}$=545 Hz.

3.88 g (0.02M) of the 1-hydroxy-1-methylheptylphosphonous acid, 3-hydroxypropionitrile (1.42 g, 0.02M) and dimethylaminopyridine (0.122 g, 0.001M) are stirred in tetrahydrofuran (75 ml) under argon at room temperature. Dicyclohexylcarbediimide (4.54 g, 0.022M) is added and the mixture is stirred for 1 hour. On completion of the reaction ($^{31}$P NMR, TLC), ether (150 ml) is added and the precipitated dicyclohexyl urea is filtered off. Evaporation of the ether liquors gives a pale yellow oil (4.9 g) which is purified by chromatography on silica using ethyl acetate as eluant to give 2-cyanoethyl (1-hydroxy-1-methylheptyl)phosphinate.

$^{31}$P NMR (CDCl$_3$, 162MHz) δ=42.9, 43.69 ppm J$_{PH}$=540 Hz.

EXAMPLE 7

A mixture of p-methylacetophenone (2.68 g. 0.02M) and hypophosphorous acid (90%, 1.45 g. 0.02M) is heated on a steam bath for 12 hours. The reaction mixture is poured into ice-water and the organic material is extracted with ethyl acetate. Evaporation and co-evaporation with toluene gives a white solid which is crystallised from chloroform/hexane. There is obtained 1-hydroxy-1-p-tolylethylphosphonous acid, m.p. 115° C.

$^{31}$P NMR (CDCl$_3$, 162 MHz) δ=38.4 ppm J$_{PH}$=540 Hz.

1-hydroxy-1-p-tolylethylphosphonous acid (0.2 g., 0.01M), 1-chloro-2-propanol (0,094 g., 0.01M) and dimethylaminopyridine (0.01 g) are stirred in tetrahydrofuran (5 ml.) at 5° C. Dicyclohexylcarbodiimide (0.23 g., 0.001M) is added portionwise over 1 hour. On completion of the reaction (monitored by $^{31}$P NMR) ether (10 ml) is added and the dicylohexylurea formed is filtered off. Evaporation of the filtrate gives an oil which is purified by chromatography on silica using 5% methanol in chloroform as eluant. There is obtained 1-chloromethylethyl (1-hydroxy-1-p-tolylethyl)phosphinate.

$^{31}$P NMR (CDCl$_3$ 162MHz) δ=41.5, 41.4, 40.5, 39.5 ppm.

EXAMPLE 8

A mixture of methyl isobutyl ketone (3.0 g 0.03M) and hypophosphorous acid (90%, 1.45 g., 0.02M) is heated on a steam bath for 8 hours. The resulting mixture is poured into water and the organic material is extracted into ethyl acetate and washed with water until no more hypophosphorous acid remains ($^{31}$P NMR). The solvent and excess of ketone are removed under vacuum and the residual oil is purified by chromatography on silica using 10% methanol in chloroform. There is obtained 1-hydroxy-1,4-dimethylbutylphosphonous acid.

$^{31}$P NMR (CDCl$_3$, 162MHz) δ=39.4ppm J$_{PH}$=550 Hz.

1-Hydroxy-1,4-dimethylbutylphosphonous acid (0.166 g., 0.001M), phenol (0.094 g., 0.001M) and dimethylaminopyridine 0.01 g.) are stirred in tetrahydrofuran (5 ml.) at 5° C. Dicyclohexylcarbodiimide (0.23 g. 0.001M) is added portionwise over 2 hours. On completion of the reaction ($^{31}$P NMR) ether (10 ml.) is added and the dicylohexyl urea formed is filtered off. Evaporation of the filtrate gives an oil which is purified on silica using 5% methanol in chloroform as eluant. There is obtained phenyl (1-hydroxy-1,4-dimethylbutyl)phosphinate.

$^{31}$P NMR (CDCl$_3$, 162 MHz) δ=41.36, 41.21, 40.87, 40.72 ppm J$_{PH}$=550 Hz.

EXAMPLE 9

1-Hydroxy-1,4-dimethylbutylphosphonous acid (0.166 g., 0.001M), cyclohexanol (0.1 g., 0.001M) and dimethylaminopyridine (0.01 g.) are stirred in tetrahydrofuran (10 ml.) at 5° C. Dicyclohexylcarbodiimide (0.23 g., 0.001M) is added portionwise over 4 hours. On completion of the reaction ($^{31}$P NMR) ether (10 ml) is added and the dicyclohexylurea formed is filtered off. The filtrate is evaporated, then co-evaporated with methanol, to give a waxy solid which is purified on silica using 5% methanol in chloroform as eluant.

There is obtained cyclohexyl (1-hydroxy-1,4-dimethylbutyl)phosphinate.

$^{31}$P NMR (CDCl$_3$, 162MHz) δ=38.7, 39.3, 39.9 ppm J$_{PH}$ 540 Hz.

EXAMPLE 10

1-Hydroxy-1,4-dimethylbutylphosphonous acid prepared as described in Example 8 (0,166 g. 0,001M), 2-methoxyethanol (0.076 g. 0,001M) and dimethylaminopyridine (0.01 g.) are stirred in THF (5 ml.) at 5° C. Dicyclohexylcarbodiimide (0.23 g., 0,001M) is added portionwise and the mixture is stirred for 3 hours. Ether (10 ml.) is added and the dicyclohexylurea is filtered off. The filtrate is evaporated and the residue is dissolved in chloroform and washed with water. Evaporation of the chloroform gives an oil which is purified on silica using ethyl acetate as eluant. There is obtained 2-methoxyethyl ( 1-hydroxy- 1, 4-dimethylbutyl)phosphinate.

$^{31}$P NMR (CDCl$_3$, 162MHz) δ=44.9, 44.5 ppm J$_{PH}$=540 Hz.

EXAMPLES 11–16

These Examples illustrate the use of compounds of formula I in synthesis, the initial reaction being between a compound of formula I and Compound A, which is an olefinic sugar acetonide of formula IX where R$^6$ is hydrogen, prepared as hereinbefore described from 1,2,5,6- di-O-isopropylidene-α-D-allofuranose.

EXAMPLE 11

This Example describes the preparation of the compound of formula

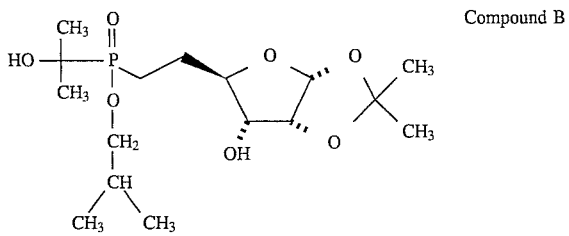

Compound B

A solution of isobutyl (1-hydroxy-1-methylethyl) phosphinate (7.22 g, 0.0403M) and t-butylcyclohexylperdicarbonate (0.5 g) in toluene (1 ml) is heated to 80° C. and stirred under argon. A solution of Compound A and t-butyl cyclohexylperdicarbonate (2 g) in toluene (4 ml) is added slowly over 30 minutes and the mixture is stirred for 4 hours. When reaction is complete (monitored by $^{31}$P nmr) the solvent is evaporated in vacuo to give a pale yellow oil. The oil is chromatographed on silica using ether, ethyl acetate and finally 5% methanol in ethyl acetate gradient as eluants. There is obtained Compound B as an oil which partly solidifies. Found C 52.7, H 8.5, P 8.7; C$_{16}$H$_{30}$O$_7$P requires C 52.6, H 8.3 P 8.5%. $^{31}$P nmr (CDCl$_3$, 162 MHz): δ56.85, 57.2 ppm.

EXAMPLE 12

This Example describes the preparation of the compound of formula

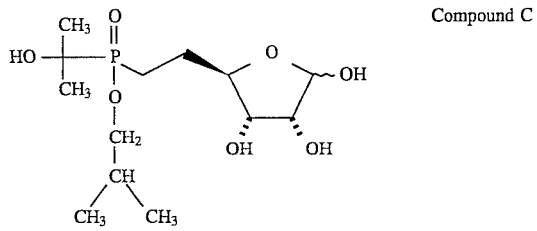

Compound C

To Compound B (8.25 g, 0.0226M) in dimethoxyethane (200 ml) is added a slurry (50 ml) of Dowex 50W x 2 (100), H$^+$ form, in water and the mixture is heated to 80° C. for 12 hours then cooled. The Dowex is removed by filtration to give a pale yellow solution. Evaporation of the solvent gives Compound C as an oil which is not purified further. $^{31}$P nmr (CD$_3$OD, 162 MHz): δ=63.2, 63.4, 64.3 and 64.4 ppm.

EXAMPLE 13

This Example describes the preparation of the compound of formula

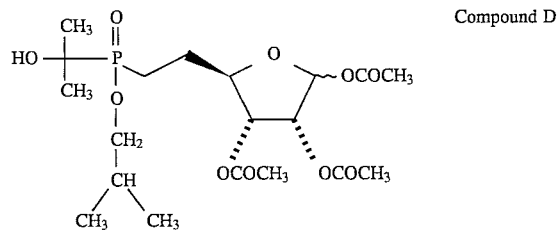

Compound D

Compound C (20 g, 0.0613M) is added to a mixture of pyridine (40 ml) and acetic anhydride (40 ml) with cooling, maintaining the temperature below 30° C. Reaction is complete in 20 minutes (Monitored by TLC). The excess of acetic anhydride and pyridine are removed by evaporation. The residual oil is dissolved in chloroform and washed with dilute hydrochloric acid, sodium bicarbonate and brine and dried over MgSO$_4$. Evaporation gives a yellow syrup which is purified by chromatography with silica. There is obtained Compound D. Found C 50.4; H 7.15, P 6.65; C$_{19}$H$_{32}$O$_{10}$P requires C 50.55, H 7.15, P 6.9%. $^{31}$P nmr (CDCl$_3$, 162 MHz): δ55.5, 55.7, 55.8 ppm.

EXAMPLE 14

This Example describes the preparation of the compound of formula

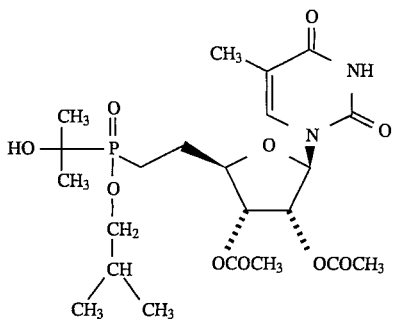

Compound E

A mixture of thymine (6.31 g, 0.05M), N, O-bis trimethylsilyl acetamide (20.34 g, 0.1M) and dichloroethane (125 ml) is heated to 80° C. under argon until a clear solution is obtained. The solution is cooled to room temperature and a solution of Compound D (22.57 g, 0.05M) in dichloroethane (75 ml) is added followed by trimethylsilyltrifluoromethane sulphonate (32.91 g, 0.125M). The reaction mixture is heated to 50° C. and stirred for 8 hours until reaction is complete (TLC). Chloroform (300 ml) and water (200 ml) are added followed by saturated sodium bicarbonate solution until the aqueous phase is neutral. The mixture is washed with chloroform (3×100 ml) and the extracts are washed with water then brine and dried (MgSO$_4$). Evaporation gives a viscous liquid which is chromatographed on silica using 5% methanol in chloroform as eluant. There is obtained a colourless oil which is dissolved in acetic acid, water and tetrahydrofuran (100 ml 3:1:1 ratio) and heated on a steam bath for 15 minutes. The solvent is removed by evaporation followed by co-evaporation with methanol then chloroform. There is obtained Compound E as a white hygroscopic solid.

Found C 50.9, H 6.9, N 5.2, P 5.9; C$_{22}$H$_{35}$O$_{10}$N$_2$P requires C 50.95, H 6.8, N 5.4, P 5.9%.

$^{31}$P nmr (CDCl$_3$, 162 MHz): δ56.0, 56.3 ppm.

EXAMPLE 15

This Example describes the preparation of the compound of formula

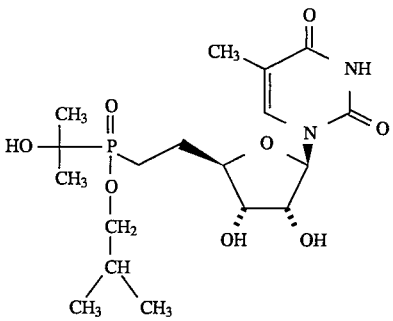

Compound F

Compound E (4.4 g, 0.0085M) dissolved in methanol (5 ml) is added to potassium carbonate (2.34 g, 0.017M) in water (5 ml) and the mixture is stirred for 15 minutes. The mixture is evaporated to dryness and the residue is stirred with acetone. The inorganic solids are removed by filtration and the acetone is evaporated to give Compound F as an oil.

$^{31}$P nmr (D$_2$O, 162 MHz): δ=63.0 ppm.

EXAMPLE 16

This Example describes the preparation of a compound of formula

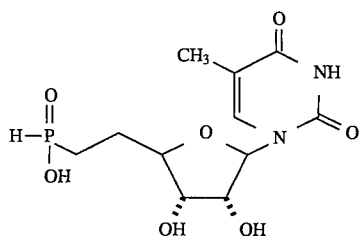

Compound G

Compound F (3.7 g) is dissolved in 10% aqueous ammonia and heated up to 80° C. for 12 hours. The mixture is cooled and evaporated to an oil which is purified on ion exchange resin Dowex 50W X 2 (100) acid form using water as eluant. There is obtained Compound G as a white foamy solid which is lyophilised to a white hygroscopic solid.

Found: C 40.9, H 5.3, N 8.3, P 9.4%; C$_{11}$H$_{17}$N$_2$O$_7$P requires C 41.25, H 5.35, N 8.75, P 9.7%.

$^{31}$P nmr (D$_2$O, 162MHz): δ36.3 ppm, J$_{PH}$=540 Hz.

What is claimed is:

1. A compound of the formula

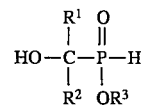

I where $R^1$ and $R^2$ are independently a $C_1$–$C_{10}$ aliphatic radical, or $R^1$ is $C_1$–$C_{10}$ alkyl or halogen-substituted $C_1$–$C_{10}$ alkyl and $R^2$ is a $C_6$–$C_{10}$ aromatic radical, and $R^3$ is a $C_1$–$C_8$ aliphatic radical, a $C_3$–$C_8$ cycloaliphatic radical, a $C_6$–$C_{15}$ aromatic radical or a $C_7$–$C_{13}$ araliphatic radical, provided that $R^3$ is not methyl when $R^1$ and $R^2$ are each methyl, that $R^3$ is not ethyl when $R^1$ and $R^2$ are each methyl, and that $R^2$ is not p-aminophenyl when $R^1$ is methyl and $R^3$ is ethyl.

2. A compound according to claim 1, in which $R^1$ and $R^2$ are independently unsubstituted or substituted $C_1$–$C_{10}$ alkyl, or $R^1$ is unsubstituted or halogen-substituted $C_1$–$C_{10}$ alkyl and $R^2$ is unsubstituted or substituted $C_6$–$C_{10}$ aryl.

3. A compound according to claim 1, in which $R^1$ and $R^2$ are independently $C_1$–$C_8$ alkyl, or $R^1$ is $C_1$–$C_8$ alkyl and $R^2$ is $C_6$–$C_8$ aryl.

4. A compound according to claim 1, in which $R^1$ and $R^2$ are each methyl or $R^1$ is methyl and $R^2$ is n-hexyl, isobutyl or p-tolyl.

5. A compound according to claim 1, in which $R^3$ is unsubstituted or substituted $C_1$–$C_8$ alkyl, $C_3$–$C_8$ cycloalkyl, $C_6$–$C_{15}$ aryl or $C_7$–$C_{13}$ aralkyl.

6. A compound accoding to claim 1, in which $R^3$ is $C_1$–$C_6$ alkyl which is unsubstituted or substituted by cyano, halogen or $C_1$–$C_4$ alkoxy, or $R^3$ is $C_5$ to $C_7$ cycloalkyl or $C_6$ to $C_8$ aryl.

7. A compound according to claim 1 in which $R^3$ is branched $C_2$–$C_6$ alkyl.

8. A compound according to claim 4, in which $R^3$ is methyl, ethyl, n-butyl, 2-cyanoethyl, 1-(chloromethyl)ethyl, 2-methoxyethyl, isobutyl, cyclohexyl or phenyl.

9. A compound according to claim 1 which is methyl(1-hydroxy-1-methylethyl)phosphinate.

10. A compound according to claim 1 which is isobutyl(1-hydroxy-1-methylethyl)phosphinate.

11. A compound according to claim 1 which is ethyl(1-hydroxy-1-methylethyl)phosphinate.

12. A compound according to claim 1 which is n-butyl(1-hydroxy-1-methylethyl)phosphinate.

13. A compound according to claim 1 which is 2-cyanoethyl(1-hydroxy-1-methylethyl)phosphinate.

14. A compound according to claim 1 which is 1-chloromethylethyl(1-hydroxy-1-p-tolylethyl)phosphinate.

15. A compound according to claim 1 which is phenyl(1-hydroxy-1,4-dimethylbutyl)phosphinate.

16. A compound according to claim 1 which is cyclohexyl(1-hydroxy-1,4-dimethylbutyl)phosphinate.

17. A compound according to claim 1 which is 2-methoxyethyl(1-hydroxy-1,4-dimethylbutyl)phosphinate.

* * * * *